United States Patent
Campbell

(10) Patent No.: US 10,065,202 B2
(45) Date of Patent: Sep. 4, 2018

(54) APPARATUS AND METHODS FOR SPRAYING A COSMETIC COMPOSITION

(71) Applicant: ARISTAN PTY LTD, Doreen, Victoria (AU)

(72) Inventor: Cameron Campbell, Thornbury (AU)

(73) Assignee: ARISTAN PTY LTD, Doreen, Victoria (AU)

(*) Notice: Subject to any disclaimer, the term of this patent is extended or adjusted under 35 U.S.C. 154(b) by 0 days.

(21) Appl. No.: 15/312,999

(22) PCT Filed: Apr. 29, 2015

(86) PCT No.: PCT/AU2015/050205
§ 371 (c)(1),
(2) Date: Nov. 21, 2016

(87) PCT Pub. No.: WO2015/176123
PCT Pub. Date: Nov. 26, 2015

(65) Prior Publication Data
US 2017/0252760 A1    Sep. 7, 2017

(30) Foreign Application Priority Data

May 19, 2014 (AU) ............................... 2014901841
Dec. 5, 2014 (AU) ............................... 2014904927

(51) Int. Cl.
*B05B 7/24* (2006.01)
*B05B 7/16* (2006.01)
*A45D 34/04* (2006.01)

(52) U.S. Cl.
CPC ............ *B05B 7/2416* (2013.01); *A45D 34/04* (2013.01); *B05B 7/1606* (2013.01)

(58) Field of Classification Search
CPC ...... B05B 7/0081; B05B 7/0416; B05B 7/066; B05B 7/1606; B05B 7/162; B05B 7/1626;
(Continued)

(56) References Cited

U.S. PATENT DOCUMENTS 2,613,995 A * 10/1952 Reinhold ................ B05B 1/304
                                                      222/468
2,736,606 A    2/1956 Kmiotek
(Continued)

FOREIGN PATENT DOCUMENTS

| GB | 604678 A | 7/1948 |
| GB | 641739 A | 8/1950 |
| WO | 2000069569 A1 | 11/2000 |

OTHER PUBLICATIONS

Mabuchi Motor Co., Ltd .RE-280RA/SA [retrieved from Internet on Jun. 3, 2015] URL:http://www.mabuchi-motor.co.jp/cgi-bin/catalog/e_catalog.cgi?CAT_ID=re_280rasa published on Feb. 14, 2014 as per Wayback Machine, Entire document.
(Continued)

*Primary Examiner* — Darren W Gorman
(74) *Attorney, Agent, or Firm* — David D. Brush; Westman, Champlin & Koehler, P.A.

(57) ABSTRACT

A hand-held apparatus for the application of a sunless tanning composition to the skin of a user. The apparatus includes: a housing, the housing enclosing: an air mover, a nozzle, and a reservoir. The reservoir and nozzle are in operable gaseous connection with the air mover such that in use, a composition in the reservoir is expelled through the nozzle to form a spray. The apparatus is useful in methods for spraying a tanning composition onto the skin of an individual.

16 Claims, 6 Drawing Sheets

(58) Field of Classification Search
CPC ... B05B 7/2402; B05B 7/2405; B05B 7/2416; A45D 34/04; A61M 35/003
See application file for complete search history.

(56) References Cited

U.S. PATENT DOCUMENTS

| | | | |
|---|---|---|---|
| 3,465,469 A * | 9/1969 | Winter | B05B 7/168 239/133 |
| 2002/0034772 A1* | 3/2002 | Orlow | A61K 8/4906 435/7.21 |
| 2004/0251272 A1 | 12/2004 | Hunter | |
| 2005/0269425 A1 | 12/2005 | Gohring et al. | |
| 2009/0152382 A1 | 6/2009 | Charpie | |
| 2010/0187328 A1* | 7/2010 | Konishi | B05B 7/0081 239/102.1 |
| 2011/0133001 A1* | 6/2011 | Cooper | A61M 35/003 239/418 |

OTHER PUBLICATIONS

International Search Report dated Jun. 29, 2015 for corresponding International Patent Application PCT/AU2015/050205 filed on Apr. 29, 2015.
Written Opinion of the International Searching Authority dated Jun. 29, 2015 for corresponding International Patent Application PCT/AU2015/050205 filed on Apr. 29, 2015.

* cited by examiner

APPARATUS AND METHODS FOR SPRAYING A COSMETIC COMPOSITION

CROSS REFERENCE TO RELATED APPLICATIONS

The present application is a Section 371 National Stage Application of International Application No. PCT/AU2015/050205, filed Apr. 29, 2015, which is incorporated by reference in its entirety and published as WO 2015/176123 A1 on Nov. 26, 2015, in English.

FIELD OF THE INVENTION

The present invention generally relates to apparatus and methods for the delivery of cosmetic composition, and more specifically but not exclusively, to the delivery of tanning solutions to the skin.

BACKGROUND TO THE INVENTION

With an increasing awareness of the dangers of sun tanning, and also sun-bed tanning, sunless tanning sprays have become very popular amongst those seeking the cosmetic advantages of a tanned skin. While commercial operations provide spray tanning services, for economic and privacy reasons many individuals prefer to perform spray tanning at home.

Various liquid sunless tanning products are available for spray-on self-application at home. However, self application of a liquid spray sunless tanning product can be difficult. Specifically, it is difficult to achieve uniform coverage of a liquid sprayed onto the skin, particularly from a pump style bottle dispenser.

Release of liquid sunless tanning products has been found to be more consistent and even when packaged with a propellant in a spray canister, such as an aerosol spray. Release with a propellant from a canister allows the liquid product to be discharged from a small atomizing nozzle to produce the desired fine disbursed mist that allows for uniform application to the skin. However, such products (being essentially disposable) are expensive.

As one example of existing spray devices is that disclosed in published United States Patent Application No. 2004/0251272 A1, which is directed to a sunless tanning spray dispenser which includes a rigid outer canister having a valve and a nozzle. A tanning solution and a propellant are housed in the canister which resembles a common aerosol can.

Apparatuses not requiring propellant have been developed for home use, however while these domestic spray tan apparatuses are generally effective, they are typically cumbersome affairs with long tubes used to convey the solution to the spray head and separate air compressors to drive the spray process. In using such prior art contrivances, the user is often restricted in his or her ability to move or ideally position the applicator, particularly during self-application. Moreover, the motorized components of existing apparatuses (such as the compressor) are typically heavy and inconvenient to move.

A further problem of in-home spray tanning apparatuses is that the compressor often requires maintenance. Some require replenishment of oil, the changing of separator elements and filters, cleaning of the heat exchanger, and the like.

Being the relatively complex contrivances, compressors are prone to failure with repairs being expensive. Where care is not taken, the air intake of the compressor can admit spray tan composition mist, this leading to a very short service life. Typically, the repair does not justify the cost and the entire compressor is often discarded with the user being required to purchase a new unit.

Spray tan apparatuses may utilize a turbine in place of a compressor. The turbine may be of the high volume low pressure (HVLP) type. While turbines generally have lower maintenance requirements than compressors, turbines are nevertheless large, heavy and expensive pieces of equipment.

Accordingly, there remains a need for a relatively inexpensive, simple, easily to manipulate yet effective apparatus for uniform spray application of a sunless tanning product to the skin.

It is an aspect of the present invention to overcome a problem of the prior art to provide an improved apparatus for the application of sunless tanning compositions. It is another aspect of the present invention to provide a useful alternative to apparatus of the prior art.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In a first aspect, but not necessarily the broadest aspect, the present invention provides hand-held apparatus for the application of a sunless tanning composition to the skin of a user, the apparatus comprising: a housing, the housing enclosing: air moving means a nozzle, and a reservoir, wherein the reservoir and nozzle are in operable gaseous connection with the air moving means such that in use, a composition in the reservoir is expelled through the nozzle to form a spray.

In one embodiment of the apparatus, the air moving means comprises an electric motor operably connected to a fan.

In one embodiment of the apparatus, the air moving means is external to the electric motor.

In one embodiment of the apparatus, the air moving means is a fan.

In one embodiment of the apparatus, the fan is a centrifugal fan or an axial fan.

In one embodiment of the apparatus, the depth of the length of the centrifugal or axial fan (along the central axis of the fan) is less than the diameter of the fan.

In one embodiment of the apparatus, the depth:diameter ratio is equal to or less than about 1:3.

In one embodiment of the apparatus, the electric motor is disposed upstream (with respect to air flow) of the air moving means.

In one embodiment of the apparatus, the electric motor has a weight of between about 50 g to about 100 g.

In one embodiment of the apparatus, the electric motor body has a diameter of between about 20 mm and about 60 mm.

In one embodiment of the apparatus, the electric motor body has a length between about 20 mm and about 60 mm In one embodiment of the apparatus, the electric motor is configured to rotate at a speed of at least about 10,000 rpm (unloaded).

In one embodiment of the apparatus, the electric motor is configured to produce a torque of between about 5 and 15 mNm.

In one embodiment of the apparatus, the electric motor is orientated such that its rotational axis is substantially horizontal when the apparatus is orientated substantially upright.

In one embodiment of the apparatus, the electric motor orientated such that at least a portion of the motor is substantially directly below the composition reservoir.

In one embodiment of the apparatus a region of the casing exposed to a supra-atmospheric air pressure or a high air velocity comprises a sealing means.

In one embodiment, the apparatus comprises a heater configured to heat air propelled by the air moving means.

In one embodiment the apparatus is configured to spray a sunless tanning composition which is a DHA-based composition and/or a tyrosine-based composition and/or a bronzer-based composition.

In one embodiment the apparatus has an overall weight (exclusive of sunless tanning composition) of less than about 500 g.

In one embodiment of the apparatus, the reservoir has a capacity of at least about 50 ml of sunless tanning composition.

In one embodiment the apparatus comprising a sunless tanning composition, or a skin whitening composition.

In a second aspect, the present invention provides a kit of parts comprising an apparatus as described herein, and instructions for use of the apparatus in applying a sunless tanning composition, or a skin whitening composition to skin.

In one embodiment the kit comprises a sunless tanning composition, or a skin whitening composition.

In a third aspect, the present invention provides a method for applying a composition to skin, the method comprising the steps of: (i) providing the apparatus as described herein, or the kit of parts as described herein, (ii) at least partially filling the reservoir of the apparatus with a composition, and (ii) actuating the electric motor of the apparatus.

In one embodiment of the method the composition is a sunless tanning composition, or a skin whitening composition.

DETAILED DESCRIPTION OF THE INVENTION

Figure 1:
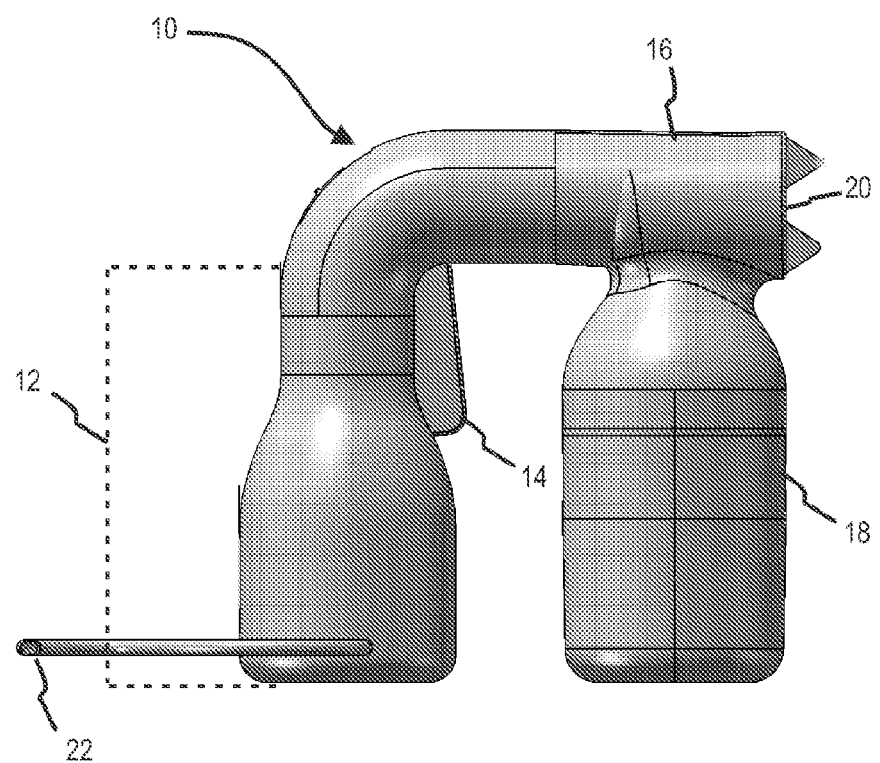
FIG. 1 is a lateral view of a preferred apparatus of the present invention.

After considering this description it will be apparent to one skilled in the art how the invention is implemented in various alternative embodiments and alternative applications. However, although various embodiments of the present invention will be described herein, it is understood that these embodiments are presented by way of example only, and not limitation. As such, this description of various alternative embodiments should not be construed to limit the scope or breadth of the present invention. Furthermore, statements of advantages or other aspects apply to specific exemplary embodiments, and not necessarily to all embodiments covered by the claims.

Throughout the description and the claims of this specification the word "comprise" and variations of the word, such as "comprising" and "comprises" is not intended to exclude other additives, components, integers or steps.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may.

The present invention is predicated at least in part on Applicant's finding that a problem of the prior art may be overcome or ameliorated by the use of a unitary, hand-held spray tanning apparatus. It has been found that such an apparatus is capable of evenly dispensing a sunless tanning composition but without the need for any hose, turbine or compressor unit. Accordingly, in a first aspect the present invention provides a hand-held apparatus for the application of a sunless tanning composition to the skin of a user, the apparatus comprising: a housing, the housing enclosing: air moving means, a nozzle, and a reservoir wherein the reservoir and nozzle are in operable gaseous connection with the air moving means such that in use, a composition in the reservoir is expelled through the nozzle to form a spray.

The present invention is a significant departure from prior art systems which use an air compressor which is connected to the spray nozzle and reservoir by a hose or other conduit. It has hitherto been unrecognized in the art that the air compressor units used in home spray tanning apparatus are over engineered, and have a capacity that is in excess of that required to achieve an acceptable sunless tan.

Applicant has been the first to recognize that air compressor is not a necessary component, and can be replaced by a motorized fan. It has been surprisingly found that a fan is capable of providing sufficient air flow and/or air pressure to cause a useful mist of composition to be propelled from a standard nozzle. By the use of a lower capacity motor to drive a compact fan it is possible to provide a spray tanning apparatus that is unitary, easy to handle, and of an acceptable weight.

As used herein, the term "unitary" in the context of the present invention is intended to mean that the housing, air moving means, nozzle and reservoir are physically interconnected to form an object which may be handled by a person as a single article. The term should not be construed narrowly to exclude any apparatus having a detachable portion, or any apparatus comprised of two or more components.

In the context of the present invention, the term "hand held" is intended to mean that the apparatus may be supported by a single adult human hand, or by two adult human hands and for a period of time sufficient for the apparatus to be reasonably used for its intended function of applying a spray tan composition.

In one embodiment of the invention the air moving means is not an air compressor, to the extent that the air moving means within itself is incapable of compressing air to a supra-atmospheric pressure. In one embodiment, the air moving means is capable of only increasing the velocity of air. The high velocity air creates a local reduction in air pressure (suction) that sunless tanning composition paint to be withdrawn from the interconnected reservoir at normal atmospheric pressure, with the composition exiting the nozzle to deposit on the skin.

It will be appreciated that the air moving means may be capable of achieving the required air velocities alone, or may be assisted by a venturi of any type to create a Venturi effect. For example the air output of the air moving means may be forced into a narrow channel on the way to the reservoir/nozzle. The narrowing of the channel decreases the cross-sectional area, with the static pressure correspondingly decreasing. According to the laws governing fluid dynamics, a fluid's velocity must increase as it passes through a constriction to satisfy the principle of continuity, while its pressure must decrease to satisfy the principle of conservation of mechanical energy. Thus any gain in kinetic energy a fluid may accrue due to its increased velocity through a constriction is negated by a drop in pressure.

A venturi of the present apparatus (where included) may be formed from the housing, for example, by an evagination of an internal surface of the housing, or by an invagination of the housing itself. In addition or alternatively, the venturi may be a dedicated structure configured to collect the air output of the air moving means, and directing the air through a narrowing channel Where no venturi is provided, the air output of the air moving means may nerveless be channeled toward the reservoir/nozzle. The channel may be formed from the housing, for example, by an evagination of an internal surface of the housing. In addition or alternatively, the channel may be a dedicated structure configured to collect the air output of the air moving means, and directing the air toward the reservoir/nozzle.

The nozzle of the present apparatus, and also the means by which the composition is drawn from the reservoir to the nozzle may be the same as those used in prior art home spray tanning machines that utilize a compressor. For example, the composition may be introduced into the flowing air by a siphon means, gravity means or side means. More typically, siphon means is used.

Performance of the apparatus may be improved where the nozzle is optimized with regards to the differing air pressures and/or air flow rates that might be encountered with the use of an air moving means of the present invention as distinct from an air compressor of the prior art. It is well within the ability of the skilled person to routinely alter nozzle parameters such as aperture diameter, shape, length, number and the like to improve performance for a particular composition. Performance improvements may include any one or more of droplet size, droplet density, flow rate, spray area, evenness of spray and the like.

A role of the air moving means is to increase the velocity of air used to expel the composition from the nozzle. In some embodiment, the air moving means is configured to accelerate air to a velocity of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 m/s. Preferably, the air moving means is configured to accelerate air to a velocity of at least about 5, 10 or 15 m/s. It will be understood that the minimum required velocity may depend on the dimension and/or geometry of any channel (with or without a venturi) used to direct the output air toward the reservoir/nozzle. Other factors may also be considered, such as the viscosity of the composition to be sprayed, characteristics of the nozzle and the like.

In one embodiment, the air moving means comprises an electric motor operably connected to a fan. The operable connection is typically via a spindle of the motor inserting into an aperture at the rotational axis of the fan. Given the hand-held nature of the apparatus, the motor and/or fan should be of light weight and small dimension. Preferably, the motor and fan are of small enough dimension so as to be locatable within a handle part of the apparatus. Furthermore, the motor and fan should be operably connected in a manner that conserves space as far as possible.

The fan may be any fan capable of accepting rotary input from an electric motor, and may of the axial flow type, the centrifugal type, or the tangential type. Preferably, the fan is of the centrifugal type. Advantageously, a centrifugal fan made be disposed within a substantially elongate handle of the apparatus and with the rotational axis of the fan being substantially parallel to the long axis of the handle. Typically, the centrifugal fan is disposed at or toward the base of the elongate handle and substantially adjacent an air inlet grill at the base of the handle. By this arrangement, air is taken into the centre of the rotating centrifugal fan and expelled laterally from the fan and into the housing.

In another advantageous embodiment, the fan is an axial fan. In such embodiments, the axial fan may be disposed toward the top of the apparatus handle, and possibly at a bend in the apparatus which provides sufficient space for the fan and associated motor. The air intake grill is typically orthogonal to the rotational axis of the fan. This arrangement is often used in the construction of hair dryers.

For reasons of space, the fan is preferably compact and may be substantially disc-shaped. This allows for the space-efficient disposition of the fan with the housing.

The electric motor of the present apparatus may any motor of suitable geometry, dimension, weight, rotational speed, or torque to be useful in the context of the present invention. Preferably, the motor is configured to be locatable within a handle of the apparatus. To facilitate that location, the motor may be substantially elongate and cylindrical such that the long axis of the motor is substantially parallel to the long axis of the long axis of the handle. This arrangement is particularly preferred where a centrifugal fan is used.

Where an axial fan is used and the rotational axis of the fan is orthogonal to the long axis of the handle, a motor being more disc-like may be used. Typically, the blades of the fan extend downwardly to surround the motor in this embodiment.

The fan may have a diameter of less than about 100, 90, 80, 70, 60 50, 40, 30, 20 or 10 mm. Typically the fan has a diameter of between about 20 mm and about 50 mm.

The fan is preferably fabricated from a light weight plastic, and may weigh less than about 20, 15, 10, 9, 8, 7, 6 or 5 g in some embodiments.

The electric motor may have a weight of less than about 200, 190, 180, 170, 160, 150, 140, 130, 120, 110, 100, 90, 80, 70, 60, 50, 40, 30, 20 or 10 g. Typically, the motor has a weight of between about 50 g to about 100 g Where the air moving means consists of an electric motor in combination with a fan, the weight of the air moving means may be less than about 250, 240, 230, 220, 210, 200, 190, 180, 170, 160, 150, 140, 130, 120, 110, and 100 g. Such weights are considerably lower than the turbines and compressors of turbines and compressors utilized in prior art spray tanning systems. The low weights of the air moving means is a feature of the present invention provides the particular advantage that the apparatus may be handheld.

The electric motor may have a diameter (where round) or a width (where not round, and orthogonal to the rotational axis) of less than about 100, 90, 80, 70, 60 50, 40, 30, 20 or 10 mm. Typically the motor has a diameter or width of between about 20 mm and about 50 mm.

In one embodiment, the motor body (i.e. not including the spindle or the terminal) has a length along the rotational axis of less than about 100, 90, 80, 70, 60 50, 40, 30, 20 or 10 mm. Typically, the motor has a length of between about 20 mm and about 60 mm.

In one embodiment, the electric motor is configured to rotate at a rate of at least about 10000, 11000, 12000, 13000, 14000, 15000, 16000, 17000, 18000, 19000, 20000, 21000, 22000, 23000, 24000, 25000, 26000, 27000, 28000, 29000 or 30000 rpm (unloaded). Typically, the electric motor is configured to rotate at a rate of between about 15000 and 25000 rpm (unloaded).

In one embodiment, the electric motor is configured to produce a torque of at least about 1, 2, 3, 4, 5, 6, 7, 8, 9, 10, 11, 12, 13, 14, 15, 16, 17, 18, 19, or 20 mNm. Typically, the electric motor is configured to produce a torque of between about 5 and 15 mNm.

Advantageously, the use of a motor/fan combination provides significant cost advantages compared with a compressor when purchasing a spray tanning apparatus. This provides significant advantage to the user given that the only alternatives before this invention were the frequenting of commercial tanning business or purchasing outright a home spray tanning kit with a compressor, both options being expensive.

Furthermore, electric motors are typically unaffected by the tanning composition mist which inevitably accompanies use of the apparatus. Even where a motor does malfunction, the cost of replacement is minimal, and certainly less than to replace a complete compressor unit of prior art apparatuses.

The air moving means (including an electric motor) may be powered by AC (for example, at mains supply 220V or 240V) or DC (for example 6V, 9V, 12V, 18V, or 24V). Where required the apparatus may comprise a step-up or step-down voltage transformer, however to maintain minimal weight it is preferred that any transformer be located external to the apparatus, such as at the mains outlet.

The apparatus may comprise means for modulating the flow rate of air output by the air moving device. Such modulation may be desirable to alter the characteristics of the spray expelled by the nozzle, or to take account of a composition that is unusually viscous or has an unusually thin consistency. Such modulation means includes the modulation of current or voltage (by a potentiometer, for example) to an electric motor which in turn will reduce the rotation rate of the fan, which will in turn will reduce the air velocity.

In one embodiment, the apparatus has an actuating switch which is typically a sprung lever which acts on an air valve. The valve is operable to open and close a channel through which air travels on its way toward the spray head. Thus, the air moving means may be constantly operating however with the air valve closed, no air is fed to the spray head and so no composition is expelled from the nozzle. When the user wishes to commence spraying he/she actuated the switch to open the air valve thereby allowing air output by the air moving means to travel to the spray head causing composition to be expelled. By this arrangement, the user does not need to wait for the air flow speed to increase to a useful speed, as would be the case if the air moving means was switched from non-operating to operating.

The apparatus may have any suitable number of nozzles and may have 1, 2, 3, 4 or 5 nozzles.

The reservoir of the apparatus is configured to hold a useful amount of sunless tanning composition, having regard to the use to which the apparatus in intended. Typically, a volume of at least about 50 ml may be held. Typically, the reservoir is attachable and removable from the apparatus to allow filling. Generally, a threaded connection is provided between the reservoir and the reminder of the apparatus to facilitate attachment and removal of the reservoir.

All or part of the apparatus housing may be fabricated from any suitably rigid material, such as metals, plastics, or synthetic resins, as are known in the art, by standard techniques for producing electrical appliances and the like. For example, the housing can be fabricated by injection molding or other suitable technique from commercially-available material such as thermo plastic polyurethane (TPU); ionomer resin; ethylene vinyl acetate (EVA); thermo plastic styrenics (TPS); melt processible rubber (MPR); thermo plastic vulcanate (TPV); thermo plastic olefin (TPO); thermo plastic ester elastomer (TPEE); thermo plastic elastomer (TPE); thermoplastic rubber (TPR); polypropylene (PP), polyethylene terephthalate (PET), polyvinyl chloride (PVC); acrylonitrile-butadiene-styrene terpolymer (ABS); a polycarbonate and acrylonitrile-butadiene-styrene copolymer blend (PC/ABS); flexible plastic such as polystyrene sheet or polymethylmethacrylate (PMMA, marketed as "PERSPEX" by ICI Acrylics, Inc.); other acrylics; metal (e.g., stainless steel, aluminum, copper); or any combination thereof. Other suitable materials and forming methods will be apparent to those skilled in the art.

Preferably, the housing is fabricated from a lightweight plastic in light of the hand-held nature of the apparatus.

The skilled person will appreciate the need to ensure the apparatus casing is sufficiently sealed so as to avoid or at least lessen the escape of any air at supra-atmospheric pressure or a high velocity as generated by the fan. In particular, regions of the casing immediately down stream from the fan are subject to air at high velocity and/or pressure and so sealing means may be used especially in these regions. For example, where the casing is formed in parts, the parts may fit together very precisely such that air loss is minimized. Alternatively a sealant may be used to seal a join in the casing, or where an electrical cord enters the casing, or in the region of any switches or other gaps between the interior and exterior of the apparatus. The sealant may be a liquid sealant (such as a silicone) dispensed onto a join during assembly. Alternatively, a preformed washer may be used where appropriate. As another example a membrane (such as a sheet plastic or an adhesive tape) may be used to lone various areas of the casing.

In one embodiment, the apparatus (without composition) has a total mass of less than about 1000, 900, 800, 700, 600, 500, 400, 300, 200, or 100 g.

The apparatus may be configured such that the components of highest mass a relatively disposed so as to easy handling of the apparatus as a whole. The motor and composition reservoir (when filled) are the two components of the apparatus having the greatest mass. In one embodiment, the motor is located so as to be substantially directly below the composition reservoir. In some embodiments, the motor is not precisely directly below, and may be disposed closer to the handle. These forms of the invention may be achieved by orientating the motor substantially horizontally, with reference to the rotational axis of the motor. In any event, such an embodiment has at least a portion of the motor directly below the reservoir.

In another aspect the present invention provides a kit of parts comprising an apparatus as described herein and instructions for use of the apparatus in applying a sunless tanning composition to skin. The kit may be provided as a vendible unit in the form of a box, or a clamshell container, or a flexible bag, for example.

The instructions of the kit may be in written, graphical, video, or audio form, or simply a URL reference to an internet website where the instructions may be obtained. The instructions may provide direction on use of apparatus for self application, or the application by a first individual on a second individual.

The kit may further comprise other articles useful in the application of sunless tanning compositions including a sunless tanning composition (such as DHA) or a skin lightening composition (such as a hydroquinone-based composition), an exfoliant, a moisturizer, a respiratory mask, a protective "tent" or "booth", a paper cap, or a paper undergarment.

In a further aspect the present invention provides a method for applying a composition to skin, the method comprising the steps of: (i) providing the apparatus described herein, or the kit of parts as described herein, (ii) at least partially filling the reservoir of the apparatus with a composition, and (ii) actuating the electric motor of the apparatus.

The method may be carried out in a commercial setting, but is preferably carried out in a domestic setting.

While the foregoing description has been directed chiefly to use of apparatus in the application of a sunless tanning composition. However, it will be appreciated that the present apparatus may be useful in the application of other compositions such as skin lightening compositions, sunscreens, tanning accelerators, moisturizers, and the like.

The present invention will now be more fully described by reference to the following preferred embodiments.

PREFERRED EMBODIMENTS OF THE INVENTION

Turning to FIG. 1 there is shown generally a unitary hand-held spray tanning apparatus 10 according to the present invention. The apparatus 10 has a handle portion 12 which encloses the motor (not shown), fan (not shown) and other electronic components (not shown). A sprung trigger 14 actuates an air control valve (not shown), with depression of the trigger opening the valve to allow air to flow to the spray head 16. A reservoir is 18 is disposed under the spray head 16. The apparatus shown in the Figure has siphon feed arrangement such that air being pumped from the handle region 12 and through the spray head 16 draws (by the resultant negative pressure) composition from the reservoir 18 into the spray head 16. The composition is expelled through two nozzles 20. The power cord is marked 22.

Figure 2:
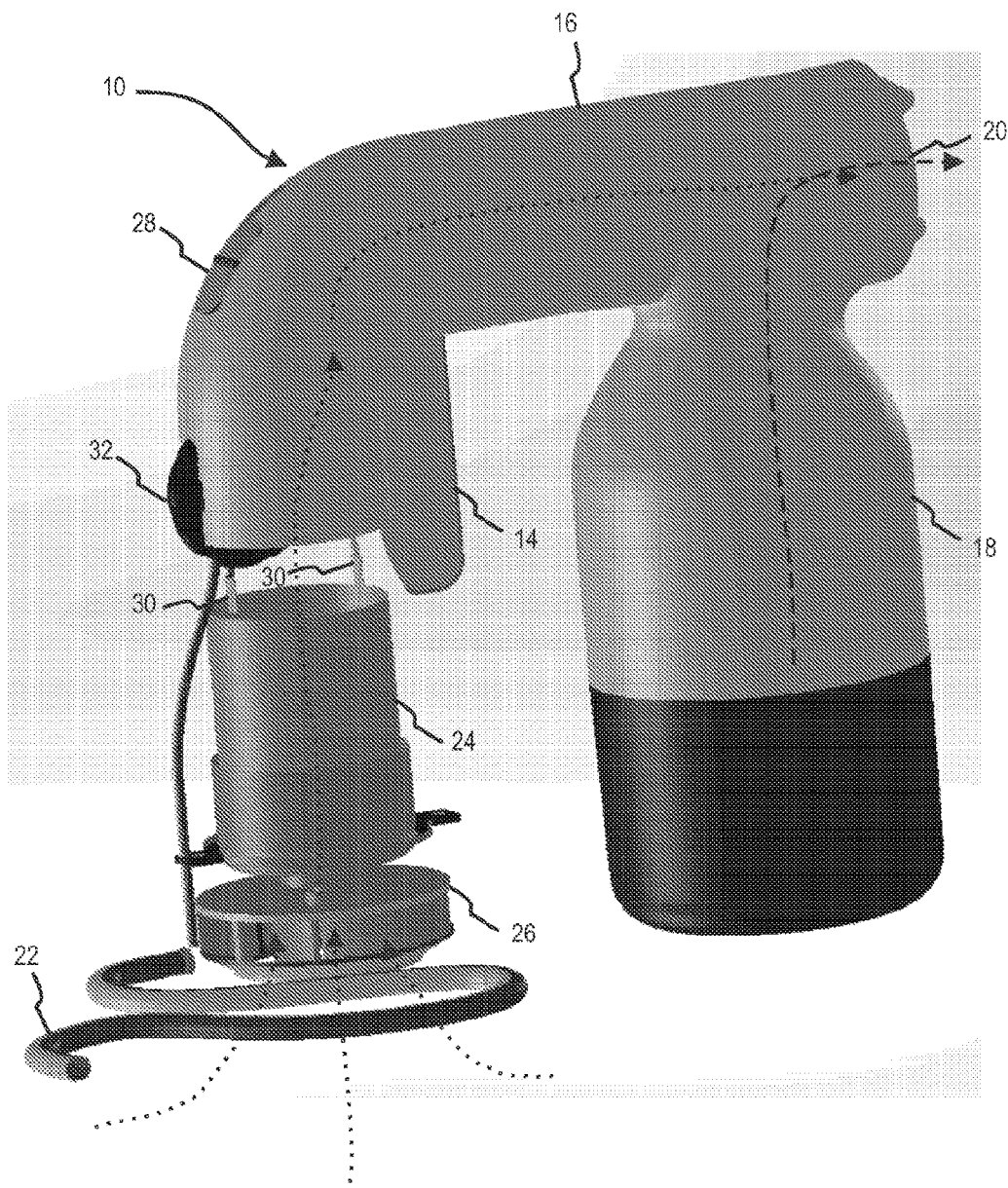
FIG. 2 is a perspective view of the apparatus of FIG. 1, having part of the external housing removed to show internal components.

Turning now to FIG. 2 there is shown internal components of the apparatus 10 being an electric motor 24 connected to a disc-like centrifugal fan 26. The motor 24 is connected to the power switch 28 by the terminals 30. The motor in this embodiment has the following specifications:
Voltage: 24V,
Wattage: 48 W,
Amperage: 2 A,
Speed: 13500/min,
Size (diameter, height): Ø27.5×38,
Weight: 75 g,
Manufacturer: Hsiang Neng #385

A continuously variable potentiometer 32 acts to modulate the rotational rate of the motor 26. The passage of air through the apparatus is not shown by the dotted arrowed lines. The movement of composition from the reservoir 18 to nozzles 20 is shown by the dashed arrowed lines. The air enters the housing through an air intake grill at the butt of the handle region (not shown).

The fan in this embodiment has the following specifications:
Dimensions of blades: Ø50 mm,
Number of blades in total: 9
Angle of blades: 25°

The nozzle in this embodiment has and aperture of: Ø7 mm

Rate of dispensation of tan solution in this embodiment is 5 ml/min.

Figure 3:
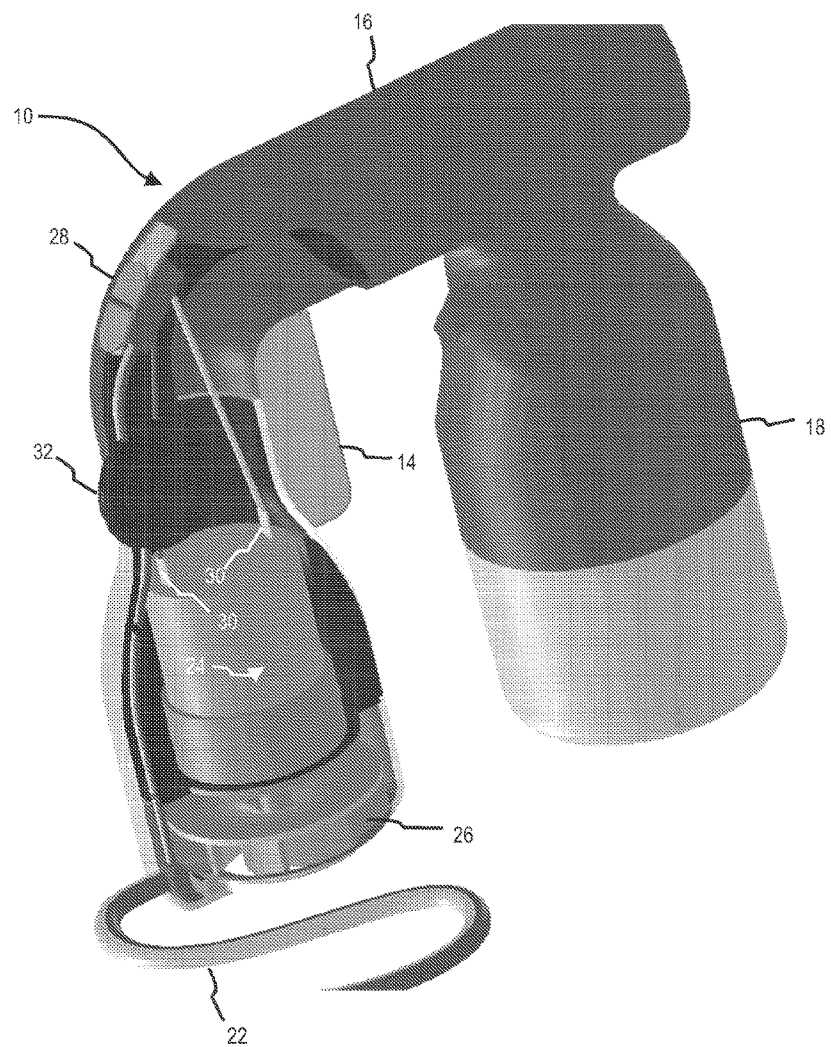
FIG. 3 is a perspective cutaway view of the apparatus of FIG. 1 showing the location of internal components with reference to the housing walls.

FIG. 3 shows the relative locations of internal parts within the housing, as assembled. It will be noted that the fan 26 and motor 24 while co-located compactly within the housing, free space is left about the these components to allow air to flow around and enter the hollow tubular region above the motor 24, which is in gaseous communication with the spray head region 16.

Figure 4:
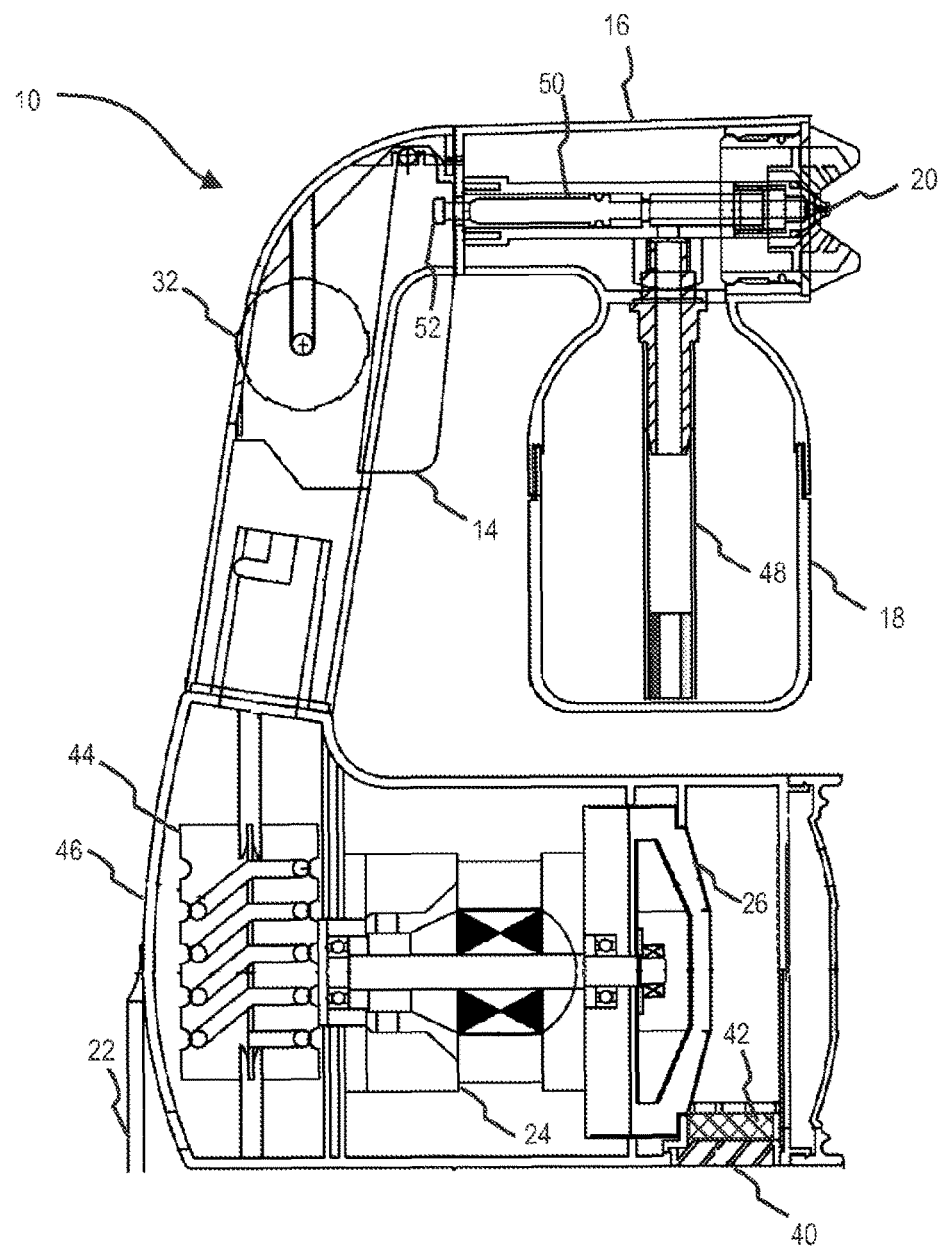
FIG. 4 is a lateral sectional view of an alternative preferred apparatus of the present invention showing the location of internal components with reference to the housing walls.
Figure 5:
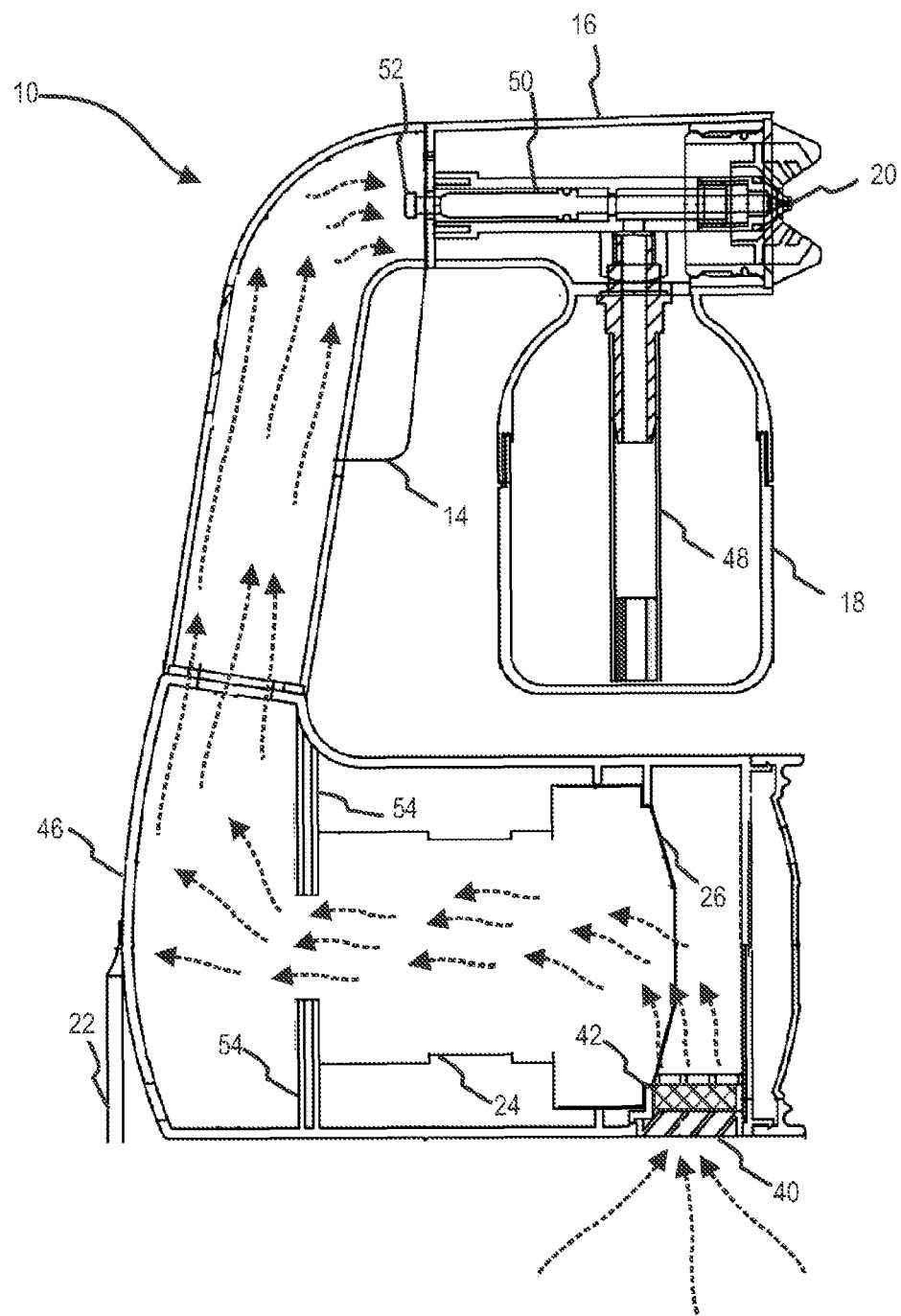
FIG. 5 is a diagrammatic view of the apparatus of FIG. 4 showing the flow of air (dashed arrowed lines) through the casing of the apparatus.
Figure 6:
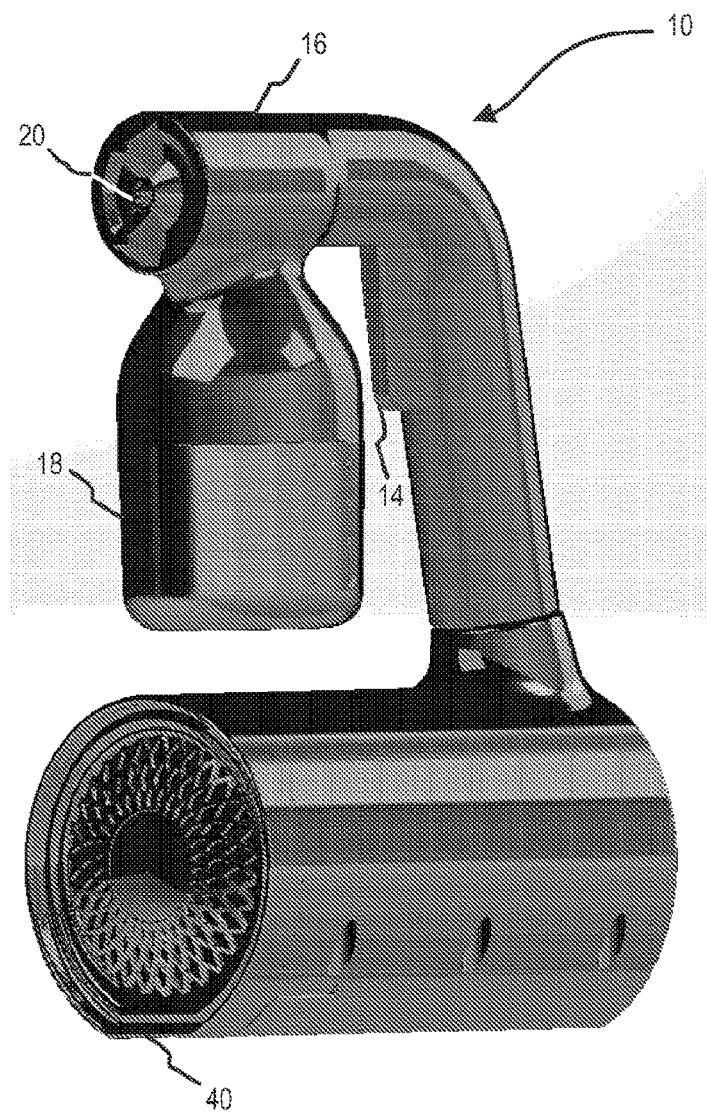
FIG. 6 is a perspective view of the apparatus of FIG. 4

An alternative embodiment of the apparatus is shown in FIGS. 4 to 6. In this alternative embodiment, the motor and fan are disposed at 90 degrees as compared with the embodiments of FIGS. 1 to 3, with reference to the rotational axis of the motor and fan. This provides an overall shorter apparatus which is generally more compact.

This embodiment comprises an elongate air intake grille 40, the long axis of the grill 40 running into the page (as drawn). A removable filtration medium 42 is disposed above the intake grille 40 to limit fouling of the motor 24, fan 25 and associated structures with environmental dust and other potential contaminants. In this preferred embodiment the filtration medium is of the tortuous path type, of which polyester and polyurethane foam are well know kinds. Other filters such as pair filters, fiber-based filters and the like are contemplated to be useful.

An air heater 44 is disposed within a lower chamber 46 of the casing. In this embodiment a resistance coil type heater of the type which is known to the skilled person is used. Heating the air use to propel tanning composition through the nozzle aperture 20 provides for an improved experience for the user. It will be appreciated that spray tanning is generally performed with the user unclothed, with the sensation of the atomized tanning composition hitting the skin causing an uncomfortable coldness on the skin. Using heating air to propel the composition ameliorates or completely overcomes the cold feeling on the user's skin occasioned by apparatus of the prior art.

In this embodiment, the siphon tube 48 is more clearly shown, and the relationship to the nozzle body 50 if further shown. Furthermore, the air entry port 52 of the nozzle body 50 is revealed in FIG. 4. The embodiment of FIGS. 1 to 3 have an identical arrangement of siphon tube, nozzle body and nozzle body port (although not shown).

Referring now to FIG. 5, there is shown the paths through which air travels through the casing and to the nozzle air inlet port 52. Air is drawn by the rotating fan (not shown) through the air intake grille 40 and through the filtration medium 42. The air is pushed through a restricted aperture formed by the walls 54 and into the lower chamber 46. The force of air against the posterior wall of the lower chamber 46 requires the use of a sealant to seal the joins in the casing halves to fully contain the fan-forced air and prevent leakage. Any leakage may cause a drop in air pressure within the casing as a whole thereby lowering the pressure and/or velocity of air about the nozzle body entry port 52. Sealant may be used in other areas of the casing as required to maintain air velocity and/or pressure within the apparatus casing.

Air entering into the entry port 52 causes a flow of high velocity air in the nozzle body 50, this in turn lowering the pressure of air above the siphon tube and drawing liquid tanning composition (not shown) into the high velocity air stream. The air/composition mixture is ejected through the nozzle aperture 20 to provide a fine spray of tanning composition (not shown).

This embodiment with the reservoir 18 disposed above the motor 26 and motor is well balanced for manual use, and is easily held and manipulated by the user. Furthermore, it is found that balance in maintained as the composition is consumed and the weight the reservoir decreases.

In this embodiment, the motor 24 is specified for used in the United States as follows: 120V, 140 W, 1.3 A, 26500 rpm, 053*92 mm, 420 g In this embodiment, the motor 24 is specified for used in Australia and the United Kingdom as follows 240V, 150 W, 0.65 A, 28000 rpm, 052*92 mm, 420 g The fan 26 has six blades of Ø62 mm/. The blade pitch is 60 degrees The nozzle aperture 20 is Ø1.2 mm Electric motors capable of operating at mains voltage a preferred given that there is no need to accommodate a transformer in the apparatus (which would add to weight), or to provide an external voltage adapter (such as a 12 V adapter) with the apparatus.

It will be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

The invention claimed is:

1. A hand-held apparatus for self-application of a sunless tanning composition to the skin of a user, the apparatus comprising:

(i) a housing enclosing:

an electric motor operably connected to a fan, an atomizing nozzle, and a reservoir configured to retain a composition, the reservoir and nozzle in operable gaseous connection with the fan such that a composition in the reservoir is expelled through the atomizing nozzle to form a spray, (ii) an elongate handle including an elongate gripping region; and (iii) a trigger positioned so as to be operable by a finger of a hand placed on the handle;

wherein when the apparatus is held in an uptight orientation, the elongate gripping region is generally vertical, the motor is lower than the handle, the reservoir and nozzle are positioned lateral to the handle, and the atomizing nozzle is positioned higher than the handle and aimed so as to direct the composition toward the user holding the elongate handle.

2. The apparatus of claim 1 wherein the fan is a centrifugal fan or an axial fan.

3. The apparatus of claim 1 wherein the electric motor has a weight of between about 50 g to about 100 g.

4. The apparatus of claim 1 wherein the electric motor has a body, which has a diameter of between about 20 mm and about 60 mm, and/or a length between about 20 mm and about 60 mm.

5. The apparatus of claim 1 wherein the electric motor is configured to rotate at a speed of at least about 10,000 rpm when unloaded.

6. The apparatus of claim 1 wherein the electric motor is orientated such that its rotational axis is substantially horizontal when the apparatus is orientated substantially upright.

7. The apparatus of claim 1 wherein the electric motor is positioned such that at least a portion of the motor is substantially directly below the composition reservoir.

8. The apparatus of claim 1 wherein a region of the housing is exposed to a supra-atmospheric air pressure or a high air velocity.

9. The apparatus of claim 1 configured to spray a sunless tanning composition which is a DHA-based composition and/or a tyrosine-based composition and/or a bronzer-based composition.

10. The apparatus of claim 1 having an overall weight of less than about 500 g, the weight being measured with the reservoir being empty.

11. The apparatus of claim 1 comprising a sunless tanning composition or a skin whitening composition.

12. A kit of parts comprising an apparatus according to claim 1 and instructions for use of the apparatus in applying at least one of a sunless tanning composition or a skin whitening composition to skin.

13. The kit of claim 12 comprising at least one of a sunless tanning composition or a skin whitening composition.

14. A method for applying a composition to skin, the method comprising:

(i) providing a hand-held apparatus for self-application of a sunless tanning composition to the skin of a user, the apparatus comprising:

(i) a housing enclosing:
- an electric motor operably connected to a fan,
- an atomizing nozzle, and
- a reservoir configured to retain a composition, the reservoir and nozzle in operable gaseous connection with the fan such that a composition in the reservoir is expelled through the atomizing nozzle to form a spray, (ii) an elongate handle including an elongate gripping region; and (iii) a trigger positioned so as to be operable by a finger of a hand placed on the handle;

wherein when the apparatus is held in an uptight orientation, the elongate gripping region is generally vertical, the motor is lower than the handle, the reservoir and nozzle are positioned lateral to the handle, and the atomizing nozzle is positioned higher than the handle and aimed so as to direct the composition toward the user holding the elongate handle, (ii) at least partially filling the reservoir of the apparatus with a composition, and (ii) actuating the electric motor of the apparatus.

15. The method of claim 14 wherein the composition is a sunless tanning composition or a skin lightening composition.

16. The method of claim 14, wherein providing the hand-held apparatus comprises:

providing a kit of parts comprising the apparatus and instructions for use of the apparatus in applying at least one of a sunless tanning composition or a skin whitening composition to skin.

* * * * *